(12) United States Patent
Honeycutt

(10) Patent No.: US 8,702,747 B2
(45) Date of Patent: Apr. 22, 2014

(54) FEMORAL REMOVAL VENA CAVA FILTER

(75) Inventor: Justin Honeycutt, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 240 days.

(21) Appl. No.: 13/279,142

(22) Filed: Oct. 21, 2011

(65) Prior Publication Data
US 2013/0103073 A1   Apr. 25, 2013

(51) Int. Cl.
*A61M 29/00*   (2006.01)

(52) U.S. Cl.
USPC ..................................................... 606/200

(58) Field of Classification Search
USPC ......... 606/127, 128, 200; 623/1.1, 1.11, 1.12, 623/1.13, 1.14, 1.15, 1.18, 1.19, 1.2, 1.21, 623/1.23
See application file for complete search history.

(56) References Cited

U.S. PATENT DOCUMENTS

| | | | |
|---|---|---|---|
| 893,055 A | 7/1908 | Conner | |
| 4,727,873 A * | 3/1988 | Mobin-Uddin | 606/200 |
| 4,832,055 A | 5/1989 | Palestrant | |
| 4,990,156 A * | 2/1991 | Lefebvre | 606/200 |
| 5,133,733 A | 7/1992 | Rasmussen et al. | |
| 5,370,657 A * | 12/1994 | Irie | 606/200 |
| 5,601,595 A * | 2/1997 | Smith | 606/200 |
| 5,810,874 A * | 9/1998 | Lefebvre | 606/200 |
| 5,976,172 A * | 11/1999 | Homsma et al. | 606/200 |
| 6,001,118 A | 12/1999 | Daniel et al. | |
| 6,146,396 A * | 11/2000 | Konya et al. | 606/159 |
| 6,231,589 B1 * | 5/2001 | Wessman et al. | 606/200 |
| 6,306,163 B1 | 10/2001 | Fitz | |
| 6,331,183 B1 * | 12/2001 | Suon | 606/200 |
| 6,368,338 B1 * | 4/2002 | Konya et al. | 606/200 |
| 6,447,530 B1 | 9/2002 | Ostrovsky et al. | |
| 6,540,722 B1 * | 4/2003 | Boyle et al. | 604/106 |
| 6,540,768 B1 | 4/2003 | Diaz et al. | |
| 6,706,054 B2 * | 3/2004 | Wessman et al. | 606/200 |
| 6,890,340 B2 * | 5/2005 | Duane | 606/200 |
| 6,890,341 B2 | 5/2005 | Dieck et al. | |
| 7,279,000 B2 * | 10/2007 | Cartier et al. | 606/200 |
| 7,344,549 B2 * | 3/2008 | Boyle et al. | 606/200 |
| 7,625,390 B2 | 12/2009 | Hendriksen et al. | |
| 7,699,867 B2 | 4/2010 | Hendriksen et al. | |
| 7,763,044 B2 | 7/2010 | Inoue | |
| 7,857,826 B2 | 12/2010 | Eskuri et al. | |
| 7,892,252 B2 | 2/2011 | Lowe | |
| 7,972,353 B2 | 7/2011 | Hendriksen et al. | |
| 8,029,529 B1 | 10/2011 | Chanduszko | |
| 8,043,322 B2 * | 10/2011 | Hendriksen et al. | 606/200 |
| 8,092,484 B2 * | 1/2012 | Kashkarov et al. | 606/200 |
| 8,105,349 B2 * | 1/2012 | Hendriksen et al. | 606/200 |

(Continued)

FOREIGN PATENT DOCUMENTS

WO   WO 00/07521   2/2000

*Primary Examiner* — Ryan Severson
*Assistant Examiner* — Jonathan W Miles
(74) *Attorney, Agent, or Firm* — Brinks Gilson & Lione

(57) ABSTRACT

An intravascular filter configured for retrieval through a patient's femoral vein and a method for retrieving the filter through the patient's femoral vein. The filter includes a plurality of struts having connected ends attached together along a longitudinal axis, a shaft disposed along the longitudinal axis and having a first end disposed with the connected ends of the struts, a first cuff slidably disposed on the shaft, and a second cuff disposed over the struts and connected to the first cuff.

15 Claims, 7 Drawing Sheets

(56) References Cited

U.S. PATENT DOCUMENTS

| | | | |
|---|---|---|---|
| 8,246,648 B2* | 8/2012 | Tekulve | 606/200 |
| 8,323,327 B2* | 12/2012 | Bei et al. | 623/1.11 |
| 2001/0025187 A1* | 9/2001 | Okada | 606/200 |
| 2002/0177872 A1* | 11/2002 | Papp et al. | 606/200 |
| 2003/0105484 A1* | 6/2003 | Boyle et al. | 606/200 |
| 2003/0130682 A1 | 7/2003 | Broome et al. | |
| 2003/0176886 A1* | 9/2003 | Wholey et al. | 606/200 |
| 2005/0131451 A1* | 6/2005 | Kleshinski et al. | 606/200 |
| 2005/0159771 A1 | 7/2005 | Petersen | |
| 2005/0267512 A1* | 12/2005 | Osborne et al. | 606/200 |
| 2005/0267513 A1 | 12/2005 | Osborne et al. | |
| 2005/0267514 A1* | 12/2005 | Osborne et al. | 606/200 |
| 2006/0069406 A1 | 3/2006 | Hendriksen et al. | |
| 2006/0100660 A1* | 5/2006 | Osborne et al. | 606/200 |
| 2007/0005095 A1 | 1/2007 | Osborne et al. | |
| 2007/0088383 A1 | 4/2007 | Pal et al. | |
| 2007/0173885 A1* | 7/2007 | Cartier et al. | 606/200 |
| 2007/0239201 A1* | 10/2007 | Phung et al. | 606/200 |
| 2010/0010534 A1 | 1/2010 | Mujkanovic | |
| 2010/0160954 A1* | 6/2010 | Osborne | 606/200 |
| 2010/0160956 A1* | 6/2010 | Hendriksen et al. | 606/200 |
| 2010/0318115 A1* | 12/2010 | Chanduszko et al. | 606/200 |
| 2011/0082492 A1* | 4/2011 | Anderson et al. | 606/200 |
| 2011/0125181 A1 | 5/2011 | Brady et al. | |
| 2011/0130785 A1* | 6/2011 | Kusleika | 606/200 |
| 2012/0083823 A1* | 4/2012 | Shrivastava et al. | 606/200 |
| 2013/0138137 A1* | 5/2013 | Molgaard-Nielsen | 606/200 |

* cited by examiner

FEMORAL REMOVAL VENA CAVA FILTER

BACKGROUND

The present invention relates to medical devices. More particularly, the invention relates to a removable intravascular filter that can be removed from the vena cava of a patient through the patient's jugular or femoral vein.

Filtering devices that are percutaneously placed in the vena cava have been available for a number of years. A need for such filtering devices arises in trauma patients, orthopedic surgery patients, neurosurgery patients, or in patients having medical conditions requiring bed rest or non-movement. Patients having such medical conditions face an increased risk of thrombosis in the peripheral vasculature, wherein thrombi break away from the vessel wall, risking downstream embolism or embolization. For example, depending on the size, such thrombi pose a serious risk of pulmonary embolism wherein blood clots migrate from the peripheral vasculature through the heart and into the lungs.

Historically, vena cava filters were considered to be permanent implants and remained implanted in the patient for life. More recently, removable vena cava filters have been developed. These filters may be removed from the patient's vena cava after the condition or medical problem that required the device has passed.

The benefits of vena cava filters, and particularly removable vena cava filters, have been well established, but improvements may be made. For example, the vast majority of the removable vena cava filters currently on the market must be removed through the patient's jugular vein. In some instances, however, removal through the patient's femoral vein is preferable to removal through the jugular vein. For example, filters sometimes shift or become stuck in a patient's vena cava. The ability to retrieve such troublesome filters from a different access point can increase the likelihood that they will be removed successfully. In addition, jugular retrieval requires that a retrieval sheath be advanced through the patient's heart, which is contraindicated in some cases. Finally, scarring at the access point is less noticeable when retrieval is initiated through the femoral vein.

It has been a challenge to design a vena cava filter suitable for removal through a patient's femoral vein.

SUMMARY OF INVENTION

The present invention generally provides an intravascular filter suitable for deployment in a patient's vena cava and retrieval via the patient's jugular or femoral vein. The invention also provides a method for retrieving the intravascular filter from the patient's vena cava through the patient's femoral vein.

In one embodiment, the present invention provides an intravascular filter having an expanded state for capturing thrombi in a patient's blood vessel and a collapsed state for removal from the patient's vasculature. The filter includes a plurality of struts, a shaft disposed along the longitudinal axis, a first cuff slidably disposed on the shaft, and a second cuff disposed over the struts and connected to the first cuff. Each strut has a connected end, a free end, and a filtering portion disposed between the connected end and the free end. The connected ends of the struts are attached together along the longitudinal axis, and the struts generally extend in a second direction from the connected ends to the free ends. The shaft has a first end disposed with the connected ends of the struts and a second end. The shaft extends in the second direction from the first end to the second end. The first cuff has a first position and a second position along the shaft, and the second position is disposed in the second direction from the first position. The second cuff has a third position and a fourth position over the struts. The second cuff is disposed in the third position when the first cuff is in the first position and in the fourth position when the first cuff is in the second position. When the second cuff is in the third position, the second cuff is disposed in a first direction relative to the filtering portions of the struts. The second cuff is disposed over the filtering portions of the struts when the second cuff is in the fourth position. Thus, the filter may be in the expanded state when the first cuff is in the first position and is in the collapsed state when the first cuff is in the second position.

In another embodiment, the present invention provides a method for retrieving an intravascular filter from a patient's vena cava through the patient's femoral vein. The method involves percutaneously inserting a retrieval assembly into the patient's vasculature through the patient's femoral vein. The retrieval assembly includes a retrieval sheath, a first control member, and a second control member. In a second step, the method involves advancing the retrieval assembly through the patient's vasculature to a retrieval position proximal to an intravascular filter constructed in accordance with the present invention in the patient's vena cava. In a third step, the method involves contacting the shaft with the first control member to stabilize the intravascular filter. In a fourth step, the method involves attaching the second control member to the first cuff. In a fifth step, the method involves retracting the second control member proximally to move the first cuff in the second direction along the shaft such that the second cuff slides over the filtering portions of the struts to collapse the intravascular filter. In a sixth step, the method involves advancing the retrieval sheath distally over the intravascular filter. In a seventh step, the method involves removing the retrieval assembly and the intravascular filter from the patient's vasculature.

Further objects, features, and advantages of the present invention will become apparent from consideration of the following description and the appended claims when taken in connection with the accompanying drawings.

BRIEF DESCRIPTION OF THE DRAWINGS

FIG. 1a is a side view of an intravascular filter in an expanded state in accordance with the principles of the present invention.

FIG. 1b is a side view of the intravascular filter of FIG. 1a illustrating the intravascular filter with its struts omitted in order to show details of the intravascular filter that are obscured by the struts in FIG. 1a.

FIG. 2b is a side view of the intravascular filter of FIG. 2a illustrating the intravascular filter with its struts omitted in order to show details of the intravascular filter that are obscured by the struts in FIG. 2a.

DETAILED DESCRIPTION

Figures 1A, 1B:
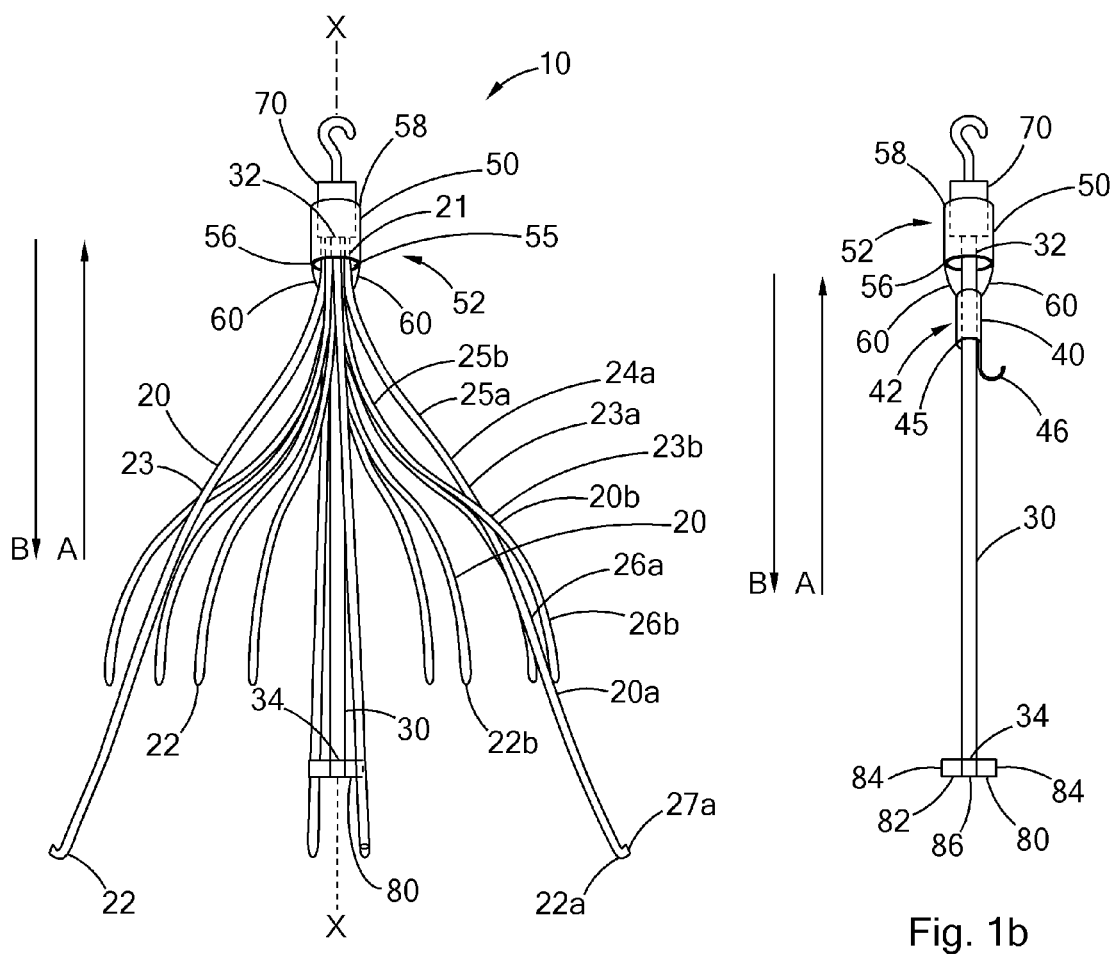

The present invention generally provides an intravascular filter suitable for deployment in a patient's vena cava and retrieval via the patient's jugular or femoral vein. The invention also provides a method for retrieving the intravascular filter from the patient's vena cava through the patient's femoral vein.

FIGS. 1*a-b* and 2*a-b* illustrate an intravascular filter 10 in accordance with the principles of the present invention. The filter 10 has an expanded state (FIG. 1*a*) for capturing thrombi in a patient's blood vessel (e.g., in the patient's vena cava) and a collapsed state (FIG. 2*a*) for removal from the patient's vasculature.

The filter 10 comprises a plurality of struts 20, a shaft 30, a first cuff 40 disposed on the shaft 30, and a second cuff 50 disposed over the struts 20 and connected to the first cuff 40. For the sake of clarity, certain elements of the filter 10 have been omitted from FIGS. 1*a-b* and 2*a-b*. More specifically, the first cuff 40 has been omitted from FIGS. 1*a* and 2*a*. The struts 20 have been omitted from FIGS. 1*b* and 2*b*.

In the following description of the filter 10, reference will be made to a first direction and a second direction. The first and second directions will be understood to be the directions indicated by the arrows A and B, respectively, in FIG. 1*a*. In subsequent figures, the same understanding of the first and second directions will apply, even if the arrows A and B do not appear in the subsequent figures.

Referring again to FIG. 1*a*, each of the struts 20 has a connected end 21, a free end 22, and a filtering portion 23 disposed between the connected end 21 and the free end 22. The connected ends 21 of the struts 20 are attached together along a longitudinal axis X of the filter 10. The struts 20 generally extend in a second direction (indicated by arrow B in FIG. 1*a*) from the connected ends 21 to the free ends 22.

The filter 10 may have any suitable number and configuration of struts 20 without falling beyond the scope or spirit of the present invention. For example, the struts 20 of the filter 10 may be configured as described in any of US Publication No. 2005/0267513 A1, US Publication No. 2007/0005095 A1, U.S. Pat. No. 7,972,353, U.S. Pat. No. 7,625,390, U.S. Pat. No. 7,699,867, US Publication No. 2006/0069406 A1, and U.S. Pat. No. 5,133,733, all of which are incorporated herein by reference in their entireties.

In one embodiment, shown in FIG. 1*a*, the plurality of struts 20 may include a plurality of primary struts 20*a* and a plurality of secondary struts 20*b* freely spaced between the primary struts 20*a*. Each primary strut 20*a* has a primary strut connected end, a primary strut free end 22*a*, and a primary strut filtering portion 23*a* disposed between the primary strut connected end and the primary strut free end 22*a*. Each primary strut filtering portion 23*a* extends arcuately along the longitudinal axis X and linearly radially to define an arcuate segment 24*a*. The arcuate segment 24*a* includes a first curved portion 25*a* and a second curved portion 26*a*. The first curved portion 25*a* extends from the primary strut connected end away from the longitudinal axis X, and the second curved portion 26*a* extends from the first curved portion 25*a* toward the longitudinal axis to the primary strut free end 22*a*. The primary strut free ends 22*a* may include anchoring hooks 27*a*, which may be integral with the arcuate segment 24*a* and have the same thickness as the arcuate segment 24*a*.

Each secondary strut 20*b* has a secondary strut connected end, a secondary strut free end 22*b*, and a secondary strut filtering portion 23*b* disposed between the secondary strut connected end and the secondary strut free end 22*b*. Each secondary strut extends freely from the secondary strut connected end to the secondary strut free end 22*b*, avoiding contact with primary struts 20*a* and other secondary struts 20*b* when the filter 10 is in the expanded state. Each secondary strut filtering portion 23*b* extends arcuately along the longitudinal axis X and linearly radially and includes a first arc 25*b* and a second arc 26*b*. The first arc 25*b* extends from the secondary strut connected end away from the longitudinal axis X. The second arc 26*b* extends from the first arc 25*b* toward the longitudinal axis X and terminates at the secondary strut free end 22*b*. Preferably, the secondary strut free ends 22*b* do not include anchoring hooks.

Preferably, the struts 20 are formed of a superelastic material, stainless steel wire, Nitinol, cobalt-chromium-nickel-molybdenum-iron alloy, cobalt-chrome alloy, or any other suitable superelastic material that will result in a self-opening or self-expanding filter.

Referring again to FIGS. 1*a-b* and 2*a-b*, the shaft 30 is disposed along the longitudinal axis X of the filter 10. The shaft 30 has a first end 32 and a second end 32. The first end 32 is disposed with the connected ends 21 of the struts 20, and the shaft 30 extends in the second direction from the first end 32 to the second end 34.

The second end 34 of the shaft 30 may be disposed in the first direction relative to, in the second direction relative to, or relatively even with the free ends 22 of the struts 20 along the longitudinal axis X. Preferably, the second end 34 of the shaft 30 is disposed in the first direction relative to the free ends 22 of the struts 20, i.e., the shaft 30 is preferably shorter than the struts 20.

The shaft 30 may have a round cross-sectional shape. However, the shaft 30 may also have any other suitable cross-sectional shape without falling beyond the scope or spirit of the present invention.

The shaft 30 may be constructed from any material known in the art to be suitable for deployment in a patient's vasculature and is preferably constructed from the same material as the struts 20.

In some embodiments, the filter 10 may include a hub 70 disposed along the longitudinal axis X. The hub may house the first end 32 of the shaft 30 and the connected ends 21 of the struts 20. The shaft 30 extends in the second direction from the hub 70 to the second end 34, while the struts 20 extend in the second direction from the hub to the free ends 22. A jugular retrieval hook 72 may extend in the first direction from the hub 70.

Figure 2A:
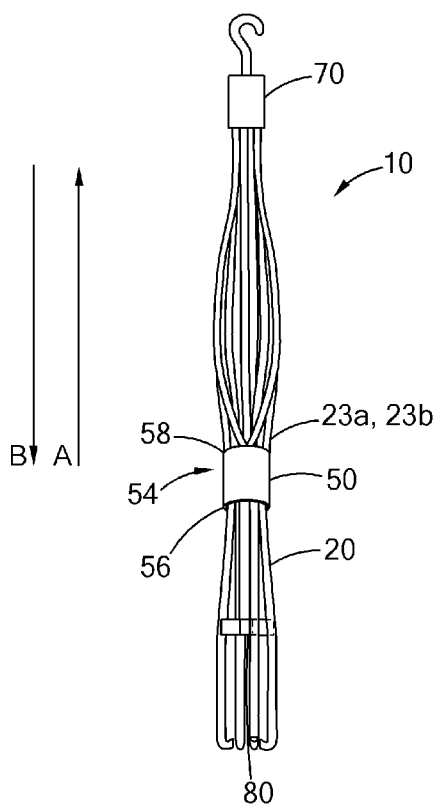
FIG. 2a is a side view of an intravascular filter in a collapsed state in accordance with the principles of the present invention.
Figure 2B:
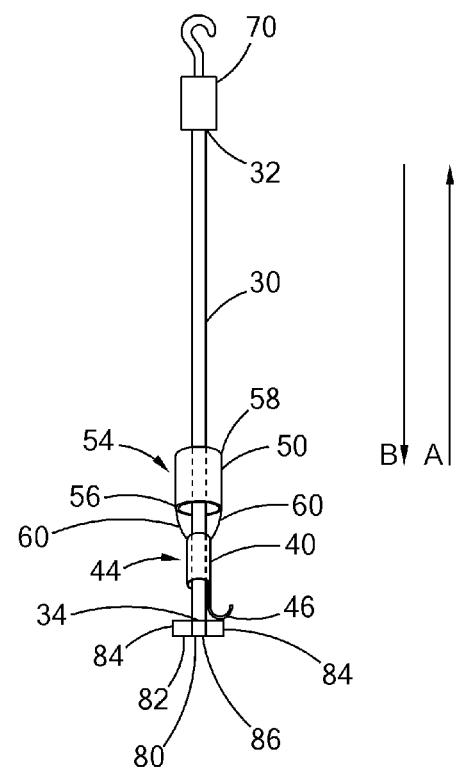

As shown in FIGS. 1b and 2b, the first cuff 40 is slidably disposed on the shaft 30. As noted above, the first cuff 40 is not shown in FIGS. 1a and 2a for the sake of clarity. The first cuff 40 may have any shape suitable for receiving and sliding along the shaft 30 without falling beyond the scope or spirit of the present invention. In some embodiments, the first cuff has a substantially cylindrical shape, and the shaft 30 passes through the volume of the cylinder.

The first cuff 40 has a first position 42 (FIG. 1b) and a second position 44 (FIG. 2b) along the shaft 30. The second position 44 is disposed in the second direction from the first position 42. In other words, the first position 42 of the first cuff 40 is closer to the first end 32 of the shaft 30, while the second position 44 of the first cuff 40 is closer to the second end 34 of the shaft 30. The first cuff 40 may be constructed from any material known in the art to be suitable for deployment in a patient's vasculature and is preferably constructed from the same material as the struts 20 and the shaft 30.

A femoral retrieval hook 46 may be disposed with the first cuff 40. The femoral retrieval hook 46 preferably allows the first cuff 40 to be pulled in the second direction along the shaft 30. The femoral retrieval hook 46 may have any structure suitable to achieve this function. For example, as shown in FIG. 1b, the first cuff 40 may have a hook end 45 oriented in the second direction. The femoral retrieval hook 46 may extend in the second direction from the hook end 45 of the first cuff 40. Alternatively, the femoral retrieval hook 46 may be disposed on the side of the first cuff 40. The femoral retrieval hook 46 may be attached to the first cuff 40 by any means known in the art or may be unitarily formed with the first cuff 40.

As shown in FIGS. 1a-b and 2a-b, the second cuff 50 is disposed over the struts 20 and is connected to the first cuff 40. The second cuff 50 may have any shape suitable for receiving the struts 20. For example, the second cuff 50 may have a cylindrical shape defining a second cuff lumen 55 that receives the struts 20. The second cuff 50 may also have a leading end 56 oriented in the second direction and a trailing end 58 oriented in the first direction. The second cuff 50 may be constructed from any material known in the art to be suitable for deployment in a patient's vasculature and is preferably constructed from the same material as the struts 20 and the shaft 30.

The second cuff 50 may be connected to the first cuff 40 by any means known in the art. Preferably, the second cuff 50 is rigidly connected to the first cuff 40, such that any movement of the first cuff 40 in the first or second direction along the shaft 30 results in an equal amount of movement of the second cuff 50 in the same direction. For example, one or more connectors 60 may extend from the second cuff 50 to the first cuff 40, passing between two struts 20. Each connector 60 may comprise a wire segment and may attach to the second cuff 50 at the leading end 56 and to the first cuff 40 at the end opposite the hook end 45, i.e., at the connector end 43. Any suitable number of connectors 60 may be present. Preferably, at least two connectors 60 are present. The connectors may be constructed from any suitable material and preferably are constructed from the same material as the first and second cuffs 40 and 50.

The second cuff has a third position (FIGS. 1a-b) and a fourth position (FIGS. 2a-b) over the struts. Because the second cuff 50 is connected to the first cuff 40, the position of the second cuff 50 depends on the position of the first cuff 40.

When the first cuff 40 is in the first position 42 (FIG. 1b), the second cuff 50 is in the third position 52. The second cuff 50 is disposed in the first direction relative to the filtering portions 23 of the struts 20 when the second cuff 50 is in the third position 52. For example, the second cuff 50 may be disposed over the connected ends 21 of the struts 20, with the connected ends 21 disposed in the second cuff lumen 55, when the second cuff 50 is in the third position 52. If the filter 10 includes a hub 70, the second cuff 50 may be disposed coaxially over the hub 70 when the second cuff 50 is in the third position 52. Thus, when the first cuff 40 is in the first position 42, and the second cuff 50 is in the second position 52, the second cuff 50 does not constrain the struts 20 along the longitudinal axis X, and the filter 10 may be in the expanded state unless otherwise constrained to the collapsed state (FIG. 1a).

When the first cuff 40 is in the second position 44 (FIG. 2b), the second cuff 50 is in the fourth position 54. In the fourth position, 54, the second cuff 50 is disposed over the filtering portions 23 of the struts 20. Thus, when the first cuff 40 is in the second position 44, and the second cuff 50 is in the fourth position 54, the filtering portions 23 of the struts 20 are constrained in the second cuff lumen 55 along the longitudinal axis X, and the filter 10 is in the collapsed state (FIG. 2a).

As shown in FIGS. 1a-b and 2a-b, the shaft 30 may have a stop 80 disposed at its second end 34. The stop 80 prevents the first cuff 40 from sliding off of the shaft 30. The stop 80 may comprise one or more cross members 82. Each cross member 82 may have two ends 84 and a midpoint 86. The second end 34 of the shaft 30 may adjoin each cross member 82 substantially at the midpoint 86 of the cross member 82. In order to prevent the first cuff 40 from sliding off of the shaft 30, it will be understood that the lengths of the cross members 82 will preferably be greater than the diameter of the first cuff 40.

Figure 3:
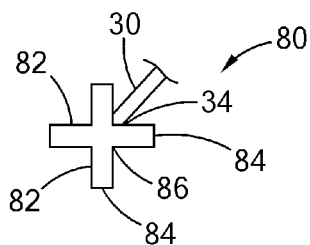
FIG. 3 is an end view of the intravascular filter of FIGS. 1a-b and 2a-b illustrating one configuration of a shaft and stop making up part of the filter.

Referring now to FIG. 3, the stop 80 may comprise two cross members 82 intersecting each other and the second end 34 of the shaft 30 substantially at their midpoints 86. In this embodiment, the cross members 82 may intersect each other substantially at right angles, such that the stop 80 has an X-shape.

In the following discussion of the deployment and retrieval of the filter 10, the terms "proximal" and "distal," and derivatives thereof, will be understood in the frame of reference of a medical practitioner deploying or retrieving the filter 10. Thus, "proximal" refers to locations closer to the practitioner, and "distal" refers to locations further from the practitioner (i.e., deeper in the patient's vasculature).

The filter 10 may be deployed in a patient's vena cava using techniques well known to those having ordinary skill in the art. A delivery tube is percutaneously inserted into the patient's vasculature and is advanced through the vasculature until the distal end of the delivery tube is at the location of deployment in the patient's vena cava. A wire guide is preferably used to guide the delivery tube to the location of deployment.

Figure 4A:
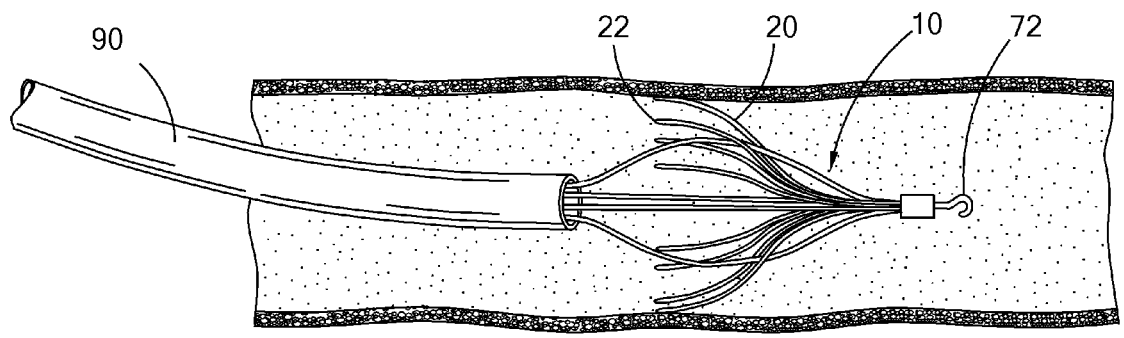
FIGS. 4a-b are environmental views illustrating the delivery of an intravascular filter to a patient's vena cava.
Figure 4B:
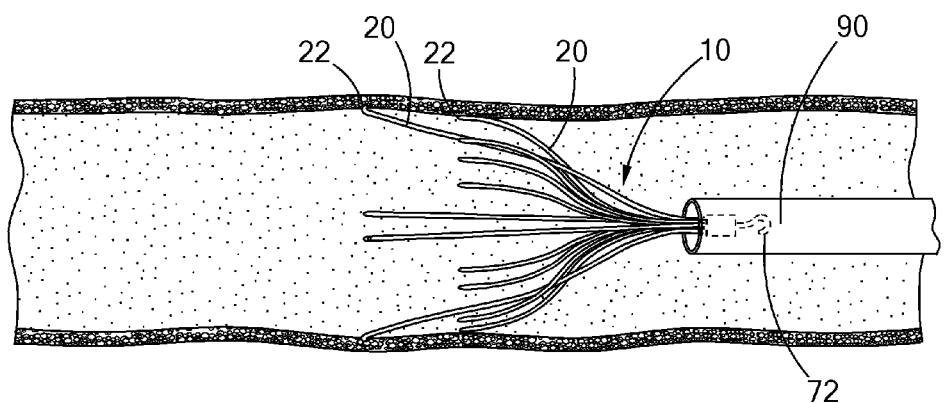

Referring to FIGS. 4a-b, the filter 10 may be delivered through a delivery tube 90 inserted into the patient's femoral vein (FIG. 4a) or jugular vein (FIG. 4b). The shaft 30, first cuff 40, and second cuff 50 have been omitted from FIGS. 4a-b for the sake of clarity and because these elements of the filter 10 are not used in the deployment of the filter 10. However, it will be understood that the first and second cuffs 40 and 50 will preferably be in the first and third positions 42 and 52, respectively, during delivery of the filter, so that the filter can self-expand to the expanded state in the patient's vena cava upon deployment from the delivery tube 90.

For femoral vein delivery (FIG. 4a), the filter 10 is inserted through the proximal end of the delivery tube 90 with the jugular retrieval hook 72 leading and the free ends 22 of the struts 20 trailing. For jugular vein delivery (FIG. 4b), the filter 10 is inserted through the proximal end of the delivery tube 90 with the free ends 22 of the struts 20 leading and the jugular retrieval hook 72 trailing. A pusher wire (not shown) may be fed through the proximal end of the delivery tube 90, pushing the filter 10 through the delivery tube 90 until the filter 10 exits the distal end of the delivery tube 90 at the location of deployment.

After the risk of embolization has passed, the filter 10 may be removed from the patient's vena cava. For example, the filter 10 may be removed through the patient's jugular vein using procedures that are well known to those having ordinary skill in the relevant art. For example, the filter 10 may be removed through the patient's jugular vein using the method described in U.S. Pat. No. 7,625,390, the entire contents of which are incorporated herein by reference.

Figure 5:
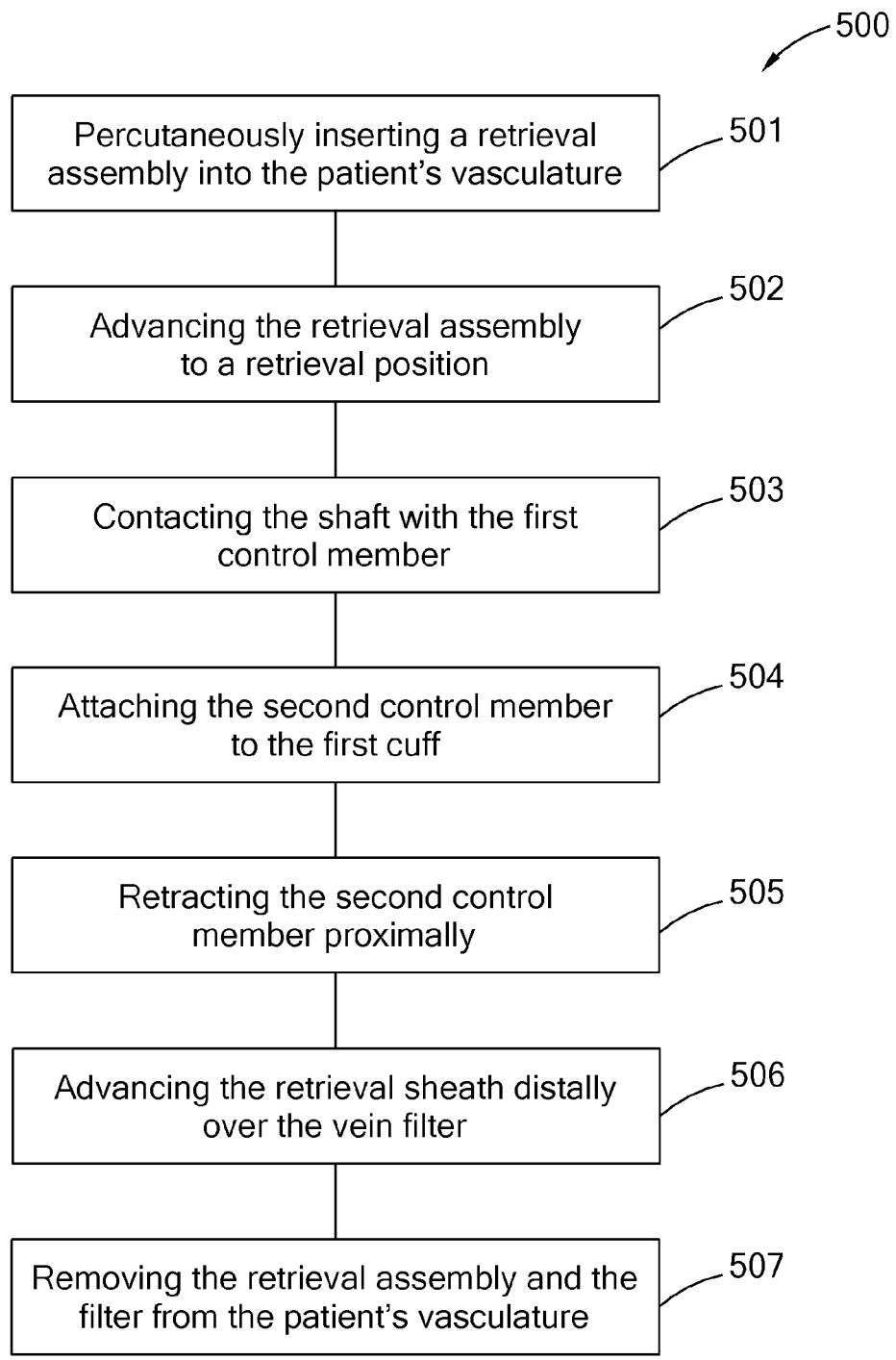
FIG. 5 is a flow chart depicting a method of retrieving an intravascular filter from a patient's vena cava through the patient's femoral vein in accordance with the principles of the present invention.

Referring now to FIG. 5, the present invention provides a method 500 for retrieving an intravascular filter from a patient's vena cava through the patient's femoral vein. The method 500 is most useful for the retrieval of the intravascular filter 10 described above with reference to FIGS. 1a-b, 2a-b, and 3, but it may be used for the retrieval of any intravascular filter without falling beyond the scope or spirit of the present invention.

Figure 6:
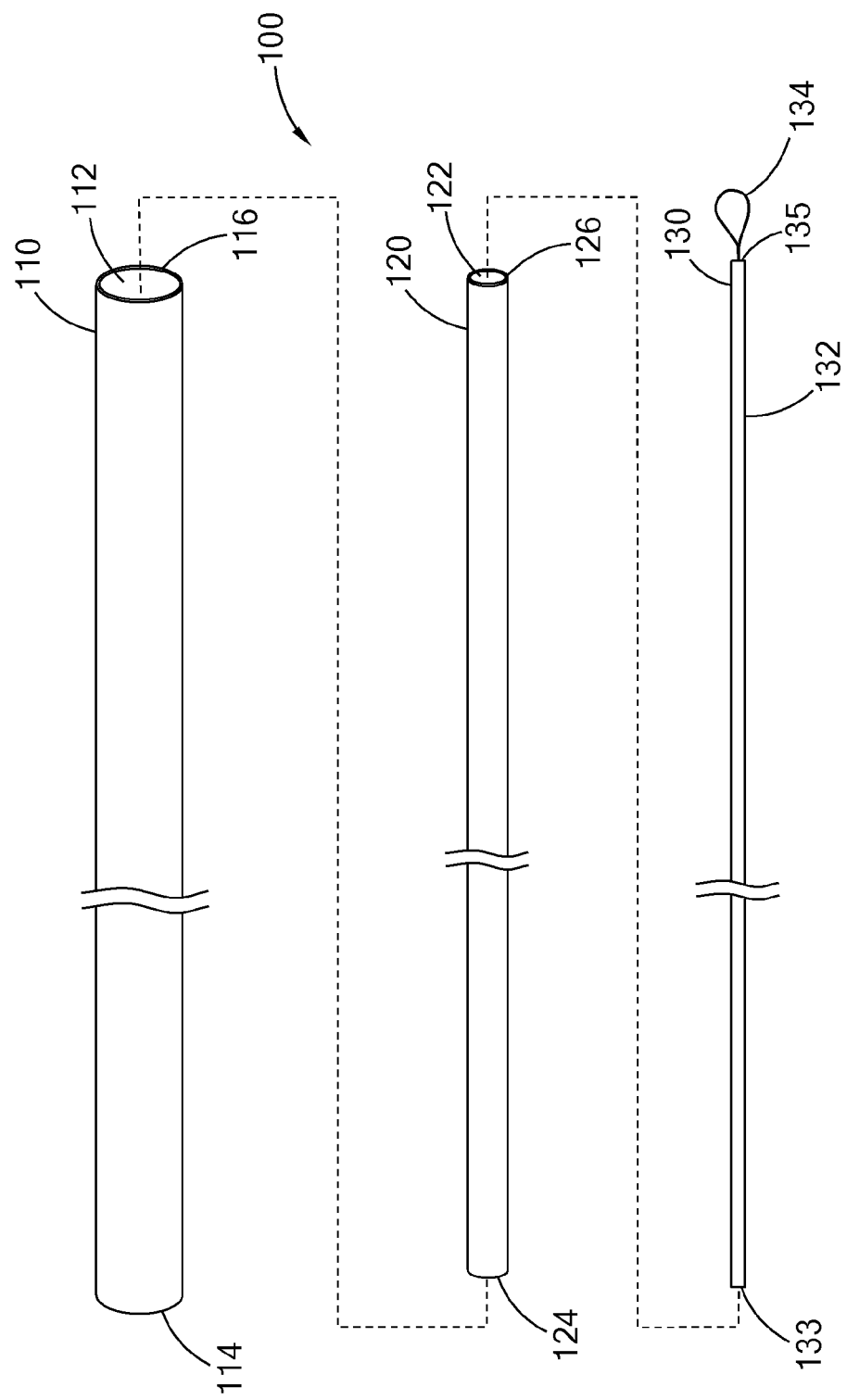
FIG. 6 is an exploded view of a retrieval assembly for retrieving the intravascular filter of the present invention from a patient's vena cava through the patient's femoral vein.

The method 500 involves the use of a retrieval assembly 100, as illustrated in FIG. 6. The retrieval assembly 100 includes a retrieval sheath 110, a first control member 120, and a second control member 130. The retrieval sheath 110 has a proximal sheath end 114, a distal sheath end 116, and a sheath lumen 112 formed therethrough. Preferably, the first control member 120 is a tubular member having a proximal tube end 124, a distal tube end 126, and a tube lumen 122 formed therethrough. Preferably, the second control member 130 comprises an elongate member 132 having a proximal access end 133 and a distal control end 135. More preferably, the second control member 130 further comprises a snare loop 134 attached to the distal control end 135 of the elongate member 132.

In use, the first and second control members 120 and 130 are preferably disposed in the sheath lumen 112 of the retrieval sheath 110. Thus, in some preferred embodiments, the first and second control members 120 and 130 may be disposed in a side by side relationship in the sheath lumen 112 of the retrieval sheath 110. More preferably, where the first control member 120 is a tubular member as described above, the first control member 120 is disposed in the sheath lumen 112 of the retrieval sheath 110, and the second control member 130 is disposed in the tube lumen 122 of the first control member 120.

As indicated in box 501, the method 500 comprises percutaneously inserting the retrieval assembly 100 into the patient's vasculature through the patient's femoral vein. The components of the retrieval assembly 100 may be inserted into the patient's vasculature in any order, or simultaneously, without falling beyond the scope or spirit of the present invention. For example, the first and second control members 120 and 130 may be disposed in the sheath lumen 112 of the retrieval sheath 110, and the entire retrieval assembly 100 may be inserted into the patient's vasculature simultaneously. Alternatively, the retrieval sheath 110 may be inserted into the patient's vasculature, and then the first and second control members 120 and 130 may be inserted into the sheath lumen 112 of the retrieval sheath 110. The components of the retrieval assembly 100 may be inserted into the patient's vasculature in any other order without falling beyond the scope or spirit of the present invention.

Figure 7:
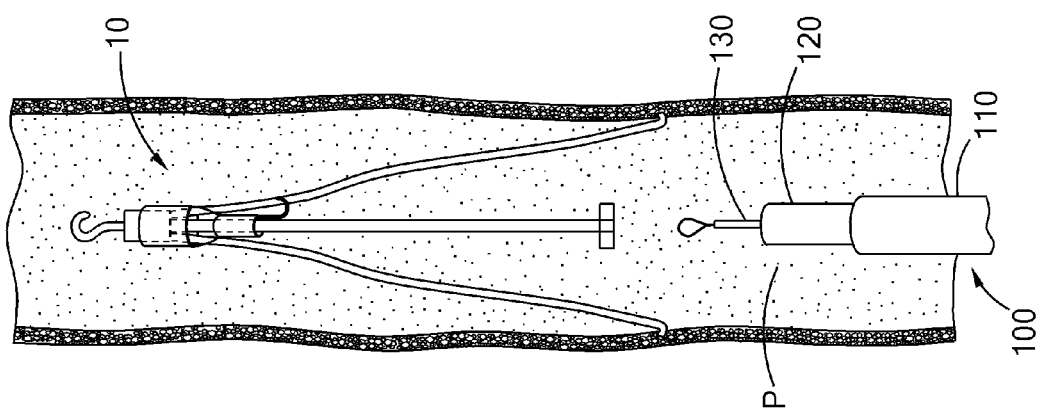
FIG. 7 is an environmental view of the retrieval assembly of FIG. 6 extending to a retrieval position proximal to the intravascular filter of the present invention. Most of the struts of the filter have been omitted from the drawing for the sake of clarity.

As indicated in box 502, and as illustrated in FIG. 7, the method 500 further comprises advancing the retrieval assembly 100 through the patient's vasculature to a retrieval position P proximal to the filter 10. As described above in connection with the step of inserting the retrieval assembly 100 into the patient's vasculature, the components of the retrieval assembly 100 may be advanced through the patient's vasculature in any order, or simultaneously, without falling beyond the scope or spirit of the present invention.

Figure 8:
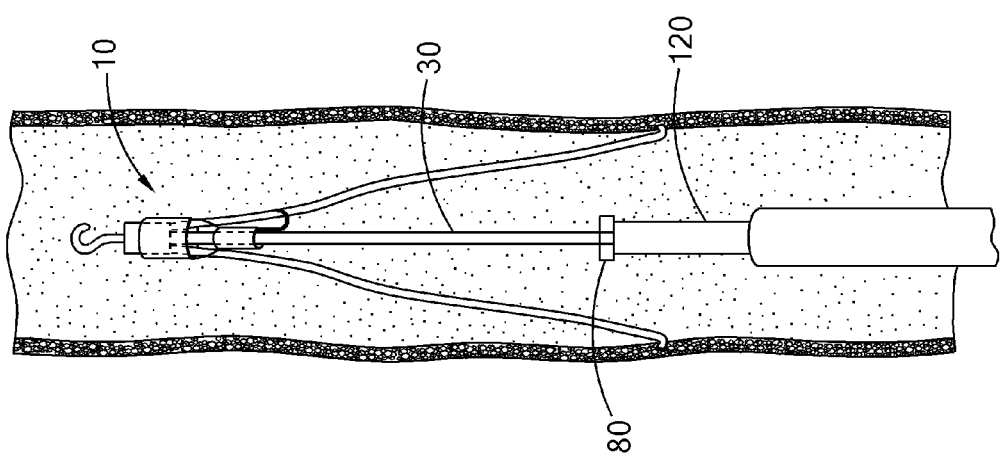
FIG. 8 is an environmental view of the retrieval assembly of FIG. 6 and the filter of the present invention in which a first control member of the retrieval assembly is contacting a shaft of the filter to stabilize the filter during retrieval. Most of the struts of the filter have been omitted from the drawing for the sake of clarity.

As indicated in box 503, and as illustrated in FIG. 8, the method 500 further comprises contacting the shaft 30 of the filter 10 with the first control member 120 to stabilize the filter 10. Preferably, the first control member 120 contacts the second end 34 of the shaft 30 so that the second control member 120 does not interfere with the movement of the first cuff along the shaft 30. The first control member 120 may contact the second end 34 of the shaft 30 in any manner suitable to stabilize the filter 10. For example, the first control member 120 may abut against the second end 34 of the shaft 30, attach onto the second end 34 of the shaft 30, or contact the shaft 30 in any other manner suitable to stabilize the filter 10.

As discussed above, some embodiments of the filter 10 comprise a stop 80 disposed at the second end 34 of the shaft. The stop 80 may comprise one or more cross members. For example, the stop 80 may comprise two cross members defining an X-shape. In these embodiments, the step of contacting the shaft 30 of the filter 10 with the first control member 120 may comprise abutting the first control member 120 against the stop 80, against the one or more cross members, or against the two cross members.

Figure 9:
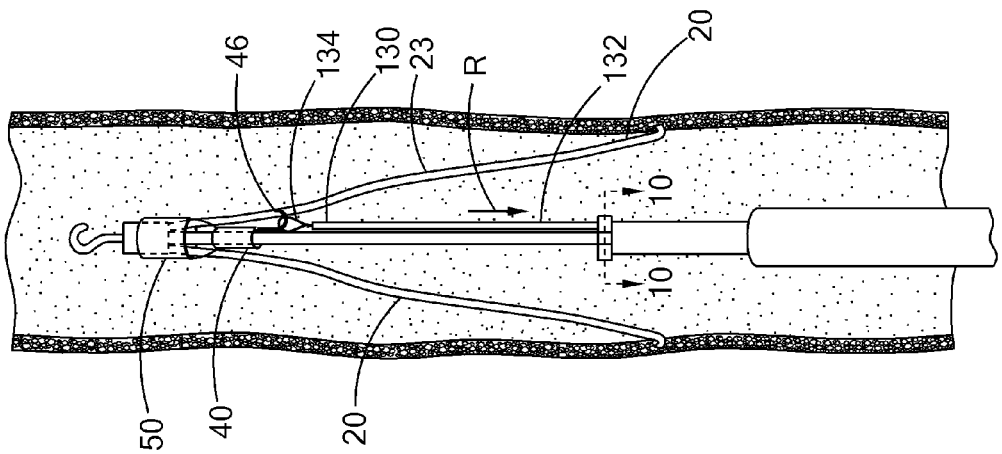
FIG. 9 is an environmental view of the retrieval assembly of FIG. 6 and the filter of the present invention in which a second control member of the retrieval assembly is attached to a first cuff of the filter during retrieval. Most of the struts of the filter have been omitted from the drawing for the sake of clarity.

As indicated in box 504, and as illustrated in FIG. 9, the method 500 further comprises attaching the second control member 130 to the first cuff 40. As discussed above, the filter 10 may include a femoral retrieval hook 46 disposed with the first cuff 40 (FIGS. 1a-b and 2a-b). Thus, if the second control member includes a snare loop 134, the step of attaching the second control member to the first cuff 40 involves placing the snare loop 134 over the femoral retrieval hook 46.

The step of attaching the second control member 130 to the first cuff 40 will preferably be performed while the first control member 120 is in contact with, and stabilizing, the shaft 30. In some embodiments, the first control member 120 will be abutted against the stop 80 at the second end 34 of the shaft 30. Thus, it is necessary to avoid disturbing the abutting relationship of the first control member 120 and the stop 80 when attaching the second control member 130 to the first cuff 40.

If the second control member 130 is disposed in the sheath lumen 112 of the retrieval sheath 110, but not in the tube lumen 122 of the first control member 120, the step of attaching the second control member 130 to the first cuff 40 generally will not disturb this abutting relationship. For example, the second control member 130 will be advanced distally out of the sheath lumen 112 towards the filter 10. The elongate member 132 of the second control member 130 will simply slide past the abutted first control member 120 and stop 80 until the snare loop 134 reaches the femoral retrieval hook 46 on the first cuff 40.

Figure 10:
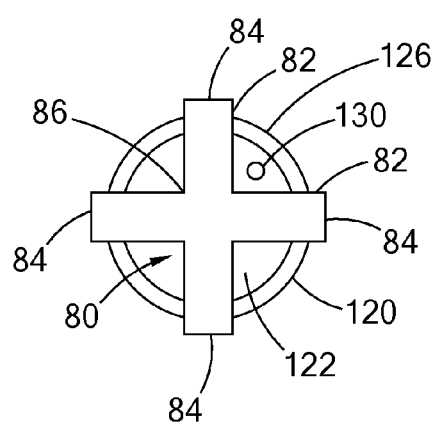
FIG. 10 is a cross-sectional view of a stop on a shaft of a filter in accordance with one embodiment of the present invention.

On the other hand, if the second control member 130 is disposed in the tube lumen 122 of the first control member 120, it is necessary to advance the second control member 130 out of the distal tube end 126 of the first control member 120 while the distal tube end 126 of the first control member 120 is abutted against the stop 80. As illustrated in FIG. 10, this may be accomplished where the stop 80 comprises one or more cross members 82. As discussed above, the one or more cross members 82 span the diameter of the first control member 120 without completely blocking the opening into the tube lumen 122 at the distal tube end 126 of the first control member 120.

FIG. 10 illustrates a cross-sectional view of the stop 80 abutted against the first control member 120. As shown in FIG. 10, if the stop 80 comprises two cross members 82, the distal tube end 126 of the first control member 120 may abut against the cross members 82, such that the cross members 82 span the diameter of the first control member 120, and the ends 84 of the cross members 82 extend outwardly beyond the diameter of the first control member 120. In this embodiment, the two cross members 82 of the stop 80 allow four openings from the tube lumen 122 of the first control member 120. Thus, the second control member 130 may be advanced distally out of the first lumen 122 through any of these four openings to attach to the first cuff.

As indicated in box 505, and as illustrated in FIG. 9, the method 500 further comprises retracting the second control member 130 proximally (i.e., in the direction of the arrow R) to move the first cuff 40 in the second direction along the shaft 30. As the first cuff 40, moves in the second direction along the shaft 30, the connected second cuff 50 moves in the second direction over the struts 20. As the second cuff 50 slides over the filtering portions 23 of the struts 20, the second cuff 50 forces the struts 20 to move toward the longitudinal axis, collapsing the filter 10. More specifically, the leading end 56 of the second cuff 50 contacts the outer surface of the struts 20 and forces the struts 20 to move toward the longitudinal axis. As the filtering portions 23 of the struts 20 move toward the longitudinal axis and the second cuff 50 moves in the second direction, the struts 20 are received in the second cuff lumen 55. With the filtering portions 23 of the struts 20 constrained along the longitudinal axis, the filter 10 is in the collapsed state (FIGS. 2a and 11).

Figure 11:
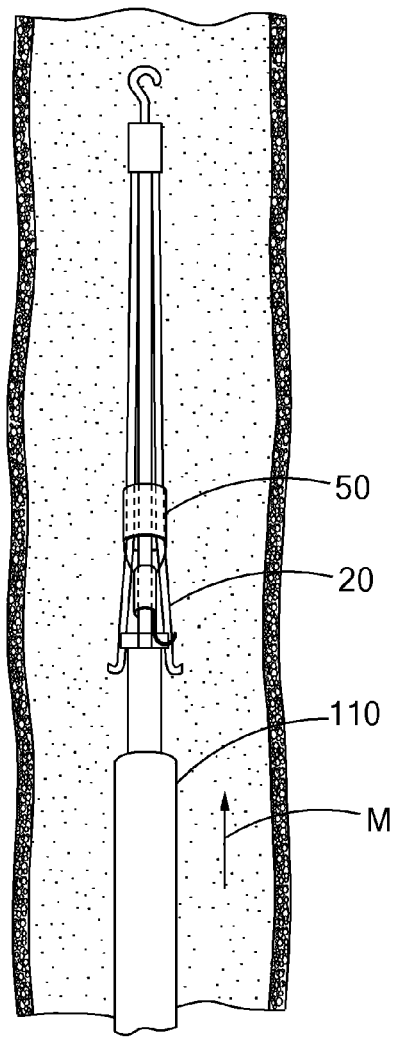
FIG. 11 is an environmental view of the retrieval assembly of FIG. 6 and the filter of the present invention in which the filter has been moved to the collapsed state by moving a second cuff over the struts of the filter. Most of the struts of the filter have been omitted from the drawing for the sake of clarity.

As indicated in box 506, and as illustrated in FIG. 11, the method 500 further comprises advancing the retrieval sheath 110 distally in the direction of the arrow M over the filter 10. When the filter 10 is in the collapsed state, as shown in FIG. 11, the filter 10 can be accommodated in the sheath lumen.

As indicated in box 507, the method 500 further comprises removing the retrieval assembly and the filter from the patient's vasculature. With the filter safely stowed in the sheath lumen, the risk of damage to the vasculature during the removal of the filter is minimized.

While the present invention has been described in terms of certain preferred embodiments, it will be understood that the invention is not limited to the disclosed embodiments, as those having skill in the art may make various modifications without departing from the scope of the following claims.

The invention claimed is:

1. An intravascular filter having an expanded state for capturing thrombi in a patient's blood vessel and a collapsed state for removal from the patient's vasculature, the filter comprising:
    a plurality of struts, each strut having a connected end, a free end, and a filtering portion disposed between the connected end and the free end, the connected ends of the struts being attached together along a longitudinal axis, the struts generally extending in a second direction from the connected ends to the free ends;
    a shaft disposed along the longitudinal axis, the shaft having a first end disposed with the connected ends of the struts and a second end, the shaft extending in the second direction from the first end to the second end;
    a first cuff slidably disposed on the shaft, the first cuff having a first position and a second position along the shaft, the second position being disposed in the second direction from the first position; and
    a second cuff disposed over the struts and connected to the first cuff, the second cuff having a third position and a fourth position over the struts, the second cuff being disposed in the third position when the first cuff is in the first position and in the fourth position when the first cuff is in the second position, the second cuff being disposed in a first direction relative to the filtering portions of the struts when the second cuff is in the third position, the second cuff being disposed over the filtering portions of the struts when the second cuff is in the fourth position, such that the filter may be in the expanded state when the first cuff is in the first position and is in the collapsed state when the first cuff is in the second position.

2. The intravascular filter of claim 1, further comprising a femoral retrieval hook disposed with the first cuff.

3. The intravascular filter of claim 1, further comprising one or more connectors extending from the first cuff to the second cuff.

4. The intravascular filter of claim 1, wherein each of the first and second cuffs has a substantially cylindrical shape.

5. The intravascular filter of claim 1, further comprising:
    a hub disposed along the longitudinal axis, the hub housing the first end of the shaft and the connected ends of the struts, the shaft extending in the second direction from the hub to the second end, the struts extending in the second direction from the hub to the free ends; and
    a jugular retrieval hook extending in the first direction from the hub.

6. The intravascular filter of claim 5, wherein the second cuff is disposed coaxially over the hub when the second cuff is in the third position.

7. The intravascular filter of claim 1, wherein the shaft has a stop disposed at its second end to prevent the first cuff from sliding off of the shaft.

8. The intravascular filter of claim 7, wherein the stop comprises one or more cross members, each cross member having two ends and a midpoint, the second end of the shaft adjoining each cross member substantially at the midpoint of the cross member.

9. The intravascular filter of claim 8, wherein the stop comprises two cross members, the cross members adjoining each other and the second end of the shaft substantially at their midpoints, such that the stop has an X-shape.

10. The intravascular filter of claim 1, wherein the plurality of struts comprises:
    a plurality of primary struts, each primary strut having a primary strut connected end, a primary strut free end, and a primary strut filtering portion disposed between the primary strut connected end and the primary strut free end, each primary strut filtering portion extending arcuately along the longitudinal axis and linearly radially to define an arcuate segment, the arcuate segment including a first curved portion and a second curved portion, the first curved portion extending from the primary strut connected end away from the longitudinal axis, the second curved portion extending from the first curved portion toward the longitudinal axis to the primary strut free end, the primary strut free end including an anchoring hook, the anchoring hook being integral with the arcuate segment and having the same thickness as the arcuate segment; and a plurality of secondary struts freely spaced between the primary struts, each secondary strut having a secondary strut connected end, a secondary strut free end, and a secondary strut filtering portion disposed between the secondary strut connected end and the secondary strut free end, each secondary strut freely extending from the secondary strut connected end to the secondary strut free end avoiding contact with other secondary struts and primary struts, each secondary strut filtering portion extending arcuately along the longitudinal axis and linearly radially, each secondary strut filtering portion including a first arc and a second arc, the first arc extending from the secondary strut connected end away from the longitudinal axis, the second arc extending from the first arc toward the longitudinal axis and terminating at the secondary strut free end without a hook.

11. A method for retrieving an intravascular filter from a patient's vena cava through the patient's femoral vein, the method comprising:
percutaneously inserting a retrieval assembly into the patient's vasculature through the patient's femoral vein, the retrieval assembly comprising a retrieval sheath, a first control member, and a second control member;
advancing the retrieval assembly through the patient's vasculature to a retrieval position proximal to the intravascular filter in the patient's vena cava, the intravascular filter comprising:
a plurality of struts, each strut having a connected end, a free end, and a filtering portion disposed between the connected end and the free end, the connected ends of the struts being attached together along a longitudinal axis, the struts generally extending in a second direction from the connected ends to the free ends;
a shaft disposed along the longitudinal axis, the shaft having a first end disposed with the connected ends of the struts and a second end, the shaft extending in a second direction from the first end to the second end;
a first cuff slidably disposed on the shaft; and
a second cuff disposed over the struts and connected to the first cuff;
contacting the shaft with the first control member to stabilize the intravascular filter;
attaching the second control member to the first cuff;
retracting the second control member proximally to move the first cuff in the second direction along the shaft such that the second cuff slides over the filtering portions of the struts to collapse the intravascular filter;
advancing the retrieval sheath distally over the intravascular filter; and
removing the retrieval assembly and the intravascular filter from the patient's vasculature.

12. The method of claim 11, wherein the shaft has a stop disposed at its second end; and wherein said contacting the shaft with the first control member to stabilize the intravascular filter comprises abutting the first control member against the stop.

13. The method of claim 12, wherein the stop comprises one or more cross members, each cross member having two ends and a midpoint, the second end of the shaft adjoining each cross member substantially at the midpoint of the cross member; and wherein said abutting the first control member against the stop comprises abutting the first control member against the one or more cross members.

14. The method of claim 13, wherein the stop comprises two cross members, the cross members adjoining each other and the second end of the shaft substantially at their midpoints, such that the stop has an X-shape; wherein said abutting the first control member against the stop comprises abutting the first control member against the two cross members.

15. The method of claim 11, wherein the intravascular filter further comprises a femoral retrieval hook disposed with the first cuff; wherein the second control member comprises an elongate member having a snare loop at its distal end; and wherein said attaching the second control member to the first cuff comprises placing the snare loop over the femoral retrieval hook.

* * * * *